United States Patent [19]

Luijpers

[11] 4,361,802

[45] Nov. 30, 1982

[54] GAS ANALYZER

[75] Inventor: Johannes G. T. Luijpers, Bunnik, Netherlands

[73] Assignee: Gould Godart B.V., Bilthoven, Netherlands

[21] Appl. No.: 185,541

[22] Filed: Sep. 9, 1980

[30] Foreign Application Priority Data

Sep. 14, 1979 [NL] Netherlands ............... 7906868

[51] Int. Cl.³ ........................................... G01R 27/02
[52] U.S. Cl. ............................... 324/65 R; 324/71 R; 324/DIG. 1
[58] Field of Search ............ 324/65 R, DIG. 1, 71 R; 73/27 R; 340/632

[56] References Cited

U.S. PATENT DOCUMENTS

| 2,565,230 | 8/1951 | Hebler | 324/71 R X |
| 3,868,846 | 3/1975 | Kushida et al. | 324/65 R X |
| 3,913,379 | 10/1975 | Rusz | 73/27 R |
| 4,057,755 | 11/1977 | Piesche | 73/27 R X |
| 4,123,934 | 11/1978 | Hoht | 324/DIG. 1 X |

FOREIGN PATENT DOCUMENTS 2374639 12/1977 France .
6710467 7/1966 Netherlands .
1372695 11/1974 United Kingdom .

*Primary Examiner*—Stanley T. Krawczewicz
*Attorney, Agent, or Firm*—Holman & Stern

[57] ABSTRACT

A gas analyzer comprising a Wheatstone bridge, consisting of resistance wires, which are provided in two mutually separated channels of a measuring block. The resistance wires of opposite legs of the bridge are contained in the same channel, wherein a reference gas may be conducted through a first one of said channels and a gas to be analyzed may be conducted through a second one of said channels. The current through the bridge is controlled during a measurement in such a manner that the resistance of the resistance wires in the second channel remains substantially constant.

3 Claims, 2 Drawing Figures

GAS ANALYZER

BACKGROUND OF THE INVENTION

The invention relates to a gas analyser comprising a Wheatstone bridge, consisting of resistance wires, which are provided in two mutually separated channels of a measuring block, wherein the resistance wires of opposite legs of the bridge are contained in the same channel, while a reference gas may be conducted through a first one of said channels and a gas to be analysed may be conducted through a second one of said channels.

The operation of such a gas analyser is based on the thermal conductivity properties of gases. The bridge is adjusted in such a manner that the temperature of the resistance wires lies above the room temperature, the bridge being balanced when the same gas mixture is conducted through both channels. When, for example, air is used as reference gas and the gas to be analysed is a mixture of air and one other gas, the output voltage of the bridge varies in dependence on the concentration of said other gas because this gas conducts heat more or less than air.

A problem of the conventional gas analysers of the type described is that the output voltage of the bridge is non-linearly dependent on the concentration of the gas to be analysed. This is caused by the fact that the thermal conductivity of gas increases with increasing temperature, whereby for gases conducting heat better than air, as for example helium, each next unit increment of concentration contributes less to the output voltage than the preceding unit increment, whereas for gases conducting heat less than air, as for example carbon dioxide, each next unit increment of concentration contributes more to the output voltage than the preceding unit increment. Therefore, the conventional gas analyser can only be used for measuring low concentrations of gas, for example up to a maximum concentration of 5%.

It has been proposed to provide a greater measuring range by applying the output voltage of the bridge, after being amplified to a suitable value, to a diode resistance circuit to linearize the output voltage. This means that the gauging characteristic of said circuit should be well reproduceable because otherwise an economic production is not possible. Further, the diode resistance circuit should always be provided with the same input voltage for a certain gas concentration. Moreover, such a linearization is only valid for one gas.

SUMMARY OF THE INVENTION

Accordingly an object of the invention is to provide a gas analyser of the above-mentioned kind, wherein the aforce-mentioned disadvantages are obviated in an effective, but nevertheless simple manner.

According to the invention the current through the bridge is controlled during a measurement in such a manner that the resistance of the resistance wires in the second channel remains substantially constant.

In this manner it is achieved that the temperature of the resistance wires changed by the gas to be analysed is brought back to the original value by changing the feeding current of the bridge, so that each next unit increment of concentration will contribute substantially the same amount to the output voltage as the preceding unit increment.

When the gas analyser according to the invention is linear for a certain gas, this applies to all types of gases, both for gases having a higher thermal conductivity than air as for gases having a lower thermal conductivity than air.

According to a simple embodiment of the invention the bridge consisting of resistance wires forms one of the legs of a second Wheatstone bridge, the feeding current of which is controlled during a measurement in such a manner that said second bridge remains balanced. In this manner it is achieved that the output voltage of the first bridge of Wheatstone is linearly dependent on the concentration of a gas for both above-mentioned types up to a concentration of approximately 25 to 30%.

For higher concentrations a non-linearity appears caused by the fact that not only the current through the resistance wires in the channel for the gas to be analysed is varied but also the current through the resistance wires in the channel for the reference gas.

According to the invention this non-linearity may substantially be eliminated by providing an embodiment, wherein the leg of the second bridge connected in series with the first Wheatstone bridge consists of a resistance, the physical properties of which correspond to those of the resistance wires of the first bridge, wherein the current per unity of cross-section for said resistance is smaller than for the total resistance of the first bridge.

BRIEF DESCRIPTION OF THE DRAWINGS

The invention will hereinafter be explained in further detail by reference to the drawings, in which an embodiment of the gas analyser according to the invention is shown.

DESCRIPTION OF A PREFERRED EMBODIMENT

Figure 1:
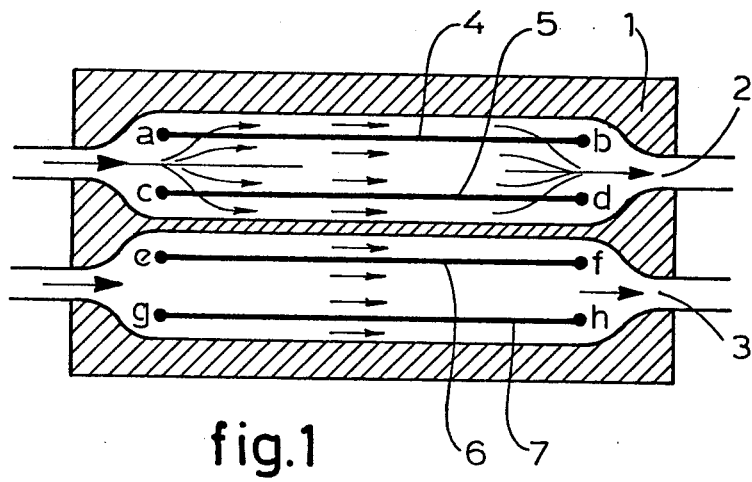
FIG. 1 is a cross-section of a measuring block which can be used in the gas analyser according to the invention.

Referring to FIG. 1 there is shown a cross-section of a measuring block 1 having a channel 2 through which a gas to be analysed can be conducted, and a channel 3 through which reference gas can be conducted. In each of said channels 2 and 3 two resistance wires 4, 5 and 6, 7, respectively, are provided; the ends a-h of said resistance wires 4-7 are accessible by means of connection pins (not shown) mounted on the outside of the measuring block 1. The measuring block 1 can, for example, be made of aluminium or brass, while the resistance wires 4-7 usually consists of platinum.

Figure 2:
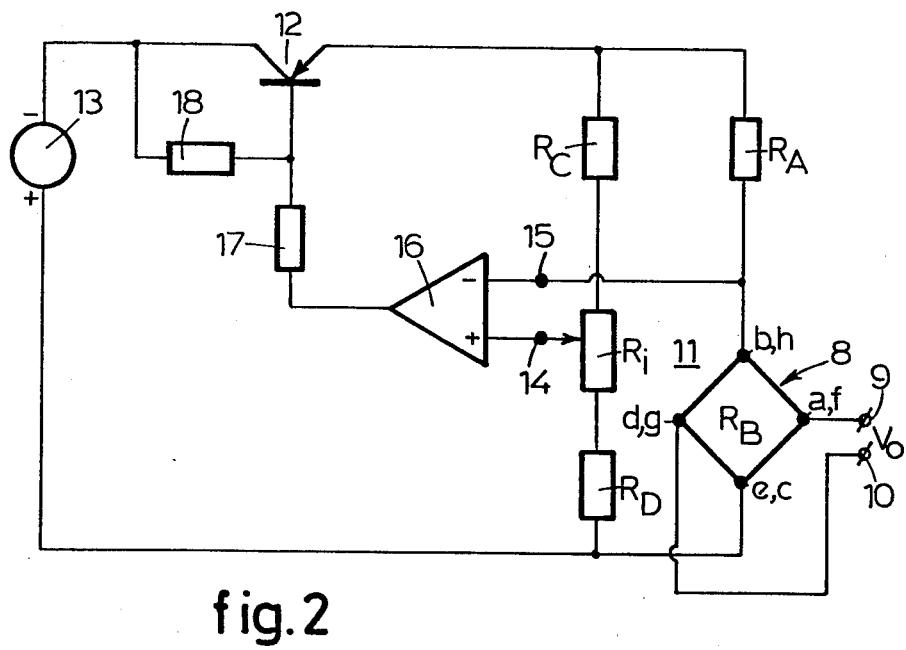
FIG. 2 shows a schematic diagram of an embodiment of the gas analyser according to the invention.

As shown in FIG. 2, the resistance wires 4-7 are connected as a Wheatstone bridge 8, wherein the resistance wires contained in the same channel are connected in opposite legs of the bridge 8. The current through the resistance wires 4-7 is such that the temperature of the wires 4-7 lies above the room temperature. The bridge 8 is adjusted in such a manner that the bridge 8 is balanced when the same gas is conducted through the channels 2 and 3, so that the voltage $V_o$ between the output terminals 9, 10 is zero.

When, for example, air is conducted through the channel 3 as a reference gas, while a mixture of air and helium is conducted through the channel 2, the resistance wires 4, 5 will cool down stronger than the resistance wires 6, 7 because helium conducts heat better than air. Thereby, the output voltage $V_o$ changes in dependence on the percentage of helium.

In order to eliminate a non-linearity of the output voltage $V_o$ caused by the fact that the thermal conductivity of gases increases with increasing temperature, the bridge 8 is connected in a second Wheatstone bridge 11 further comprising resistances $R_A$, $R_C$, $R_D$ and $R_i$, wherein the total resistance of the bridge 8 is shown as $R_B$. The bridge 11 is balanced during the measurement by controlling the bridge current. Thereby, the resistance $R_B$ remains substantially constant and the temperature of the resistance wires 4, 5 changed by the effect of the gas to be measured is brought back to the original value.

As shown in FIG. 2 the bridge 11 is connected to a d.c.- source 13 through a transistor 12 used as controlling means for the bridge current. The outputs 14, 15 of the bridge 11 are connected to a differential amplifier 16, the output of which is connected to the base of transistor 12 through a resistance 17. A resistance 18 is connected between the collector and the base of the transistor 12.

For a right operation of the circuit, the resistance $R_B$ should be adjusted in the non-linear part of the voltage-current characteristic of the bridge 8. The adjustment is carried out in a simple manner because the resistance $R_i$ is a potentiometer, the wiper of which forms the output 14 of the bridge 11.

With a practical embodiment of the described gas analyser good results are obtained up to a gas concentration of 25 to 30%. For higher concentrations a non-linearity appears because not only the current through the resistance wires 4, 5 is changed but also the current through the resistance wires 6, 7. This non-linearity can be eliminated by giving the resistance $R_A$ the same physical properties as the resistance $R_B$, for example by making resistance $R_A$ of the same material as $R_B$, wherein the current through $R_A$ per unity of cross-section should be smaller than for $R_B$. In this manner a linear measurement result can be obtained up to a concentration of approximately 80%.

If the described gas analyser is linear for one certain gas, this applies to all gases. The gas analyser can then be used both for gases having a higher thermal conductivity than air, such as $H_2$, He, $O_2$, $N_2O$, as for gases having a lower thermal conductivity than air, such as Ar, $CO_2$ and $N_2$.

Of course, a suitable amplifier circuit can be connected to the output terminals 9, 10 of the bridge 8, which amplifier circuit amplifies the output voltage $V_o$ to a value usable for further processing and/or indication by means of an indicator. This amplifier circuit may also contain adjusting means for adjusting the output signal of the amplifier circuit to zero when a reference gas is conducted through both channels 2 and 3.

The invention is not restricted to the embodiments described hereinabove, which can be varied in a number of ways within the scope of the invention.

I claim:

1. A gas analyser comprising a measuring block having two mutually separated channels, a first of said channels being adapted for conducting a reference gas therethrough and a second of said channels being adapted for conducting a gas to be analysed therethrough, a first Wheatstone bridge consisting of resistance wires provided in said two channels of the measuring block, the resistance wires of opposite legs of the first bridge being connected in the same channel, a second Wheatstone bridge, wherein the first Wheatstone bridge forms one leg of said second Wheatstone bridge, and means for controlling feeding current for said second Wheatstone bridge to maintain said second Wheatstone bridge balanced, wherein the leg of said second Wheatstone bridge connected in series with the first Wheatstone bridge consists of a resistance, the physical properties of which correspond to those of the resistance wires of said first Wheatstone bridge, the current per unity of cross-section for said resistance being smaller than for the total resistance of said first Wheatstone bridge.

2. A gas analyser according to claim 1, wherein said means for controlling include a differential amplifier having two inputs connected to the output terminals of the second Wheatstone bridge and controlling means for the feeding current of said second Wheatstone bridge, said controlling means being connected to the output of said differential amplifier.

3. A gas analyser according to claim 2, wherein one of the output terminals of the second Wheatstone bridge consists of a tapping point of a potentiometer connected in said second bridge.

* * * * *